United States Patent
Soehnel et al.

(10) Patent No.: US 9,410,900 B2
(45) Date of Patent: Aug. 9, 2016

(54) INFRARED DETECTOR DEVICE INSPECTION SYSTEM

(71) Applicant: Sandia Corporation, Albuquerque, NM (US)

(72) Inventors: Grant Soehnel, Albuquerque, NM (US); Daniel A. Bender, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 6 days.

(21) Appl. No.: 14/689,167

(22) Filed: Apr. 17, 2015

(65) Prior Publication Data

US 2015/0338352 A1 Nov. 26, 2015

Related U.S. Application Data

(60) Provisional application No. 62/001,886, filed on May 22, 2014.

(51) Int. Cl.
*G01N 21/00* (2006.01)
*G01N 21/95* (2006.01)
*G01N 21/64* (2006.01)

(52) U.S. Cl.
CPC ............ *G01N 21/95* (2013.01); *G01N 21/64* (2013.01); *G01N 21/6489* (2013.01); *G01N 21/6408* (2013.01); *G01N 2021/9511* (2013.01); *G01N 2201/0697* (2013.01)

(58) Field of Classification Search
CPC combination set(s) only.
See application file for complete search history.

(56) References Cited

PUBLICATIONS

Soehnel, G., "Time resolved photo-luminescent decay characterization of mercury cadmium telluride focal plane arrays," Optics Express, vol. 23, Issue 2 (2015), pp. 1256-1264.
Soehnel, G., "Time Resolved Photo-luminscent Decay Measurements of Infrared Materials," SENSIAC Military Sensing Symposium, Sep. 2014, 14 pages.

*Primary Examiner* — Tri T Ton
(74) *Attorney, Agent, or Firm* — Yee & Associates, P.C.

(57) ABSTRACT

Methods and apparatuses for identifying carrier lifetimes are disclosed herein. In a general embodiment, a beam of light is sent to a group of locations on a material for an optical device. Photons emitted from the material are detected at each of the group of locations. A carrier lifetime is identified for each of the group of locations based on the photons detected from each of the group of locations.

23 Claims, 11 Drawing Sheets

INFRARED DETECTOR DEVICE INSPECTION SYSTEM

RELATED PROVISIONAL APPLICATION

This application is related to and claims the benefit of priority of provisional U.S. patent application Ser. No. 62/001,886, filed May 22, 2014, entitled "Carrier Lifetime Mapping Measurement for Infrared Detectors", which is incorporated herein by reference.

STATEMENT OF GOVERNMENTAL INTEREST

This invention was made with United States Government support under Contract No. DE-AC04-94AL85000 between Sandia Corporation and the United States Department of Energy. The United States Government has certain rights in this invention.

BACKGROUND INFORMATION

1. Field

The present disclosure relates generally to sensors and, in particular, to a method and apparatus for inspecting infrared sensors. Still more particularly, the present disclosure relates to a method and apparatus for inspecting materials for infrared sensors.

2. Background

Optical detector devices are hardware that respond to light. For example, an infrared focal plane array (FPA) is a type of infrared detector device that generates images using infrared light. These infrared detector devices include materials that generate signals when exposed to infrared light, and circuits that process the signals.

The infrared focal plane array functions by absorbing photons in a material. The absorption of the photons results in signals being generated based on the carriers that are detected in the material. These signals are used to form images.

The photons absorbed in the material cause the formation of carriers in the material. Carriers are electron-hole pairs. For example, when a photon is absorbed in the material, an electron in a valance band in the material may gain energy and jump to a conduction band leaving a hole in the valence band to form a carrier. These carriers may be detected to create signals used to form an image.

A circuit connected to the material detects a voltage caused by the carriers. Based on the detection of the voltage generated by the carriers, signals may be generated by the circuit to form the image.

The carriers have a lifetime during which the carriers are present before recombination occurs. Recombination occurs when an electron fills the hole. For example, collisions between at least two electrons in a conduction band may result in one of the electrons recombining in the valence band. This type of recombination is an auger recombination. Radiative recombination is another type of recombination that involves band to band recombination. The length of time during which a carrier exists before recombination is referred to as a carrier lifetime.

In some cases, recombination may occur before the carriers can be detected and before the signals can be generated. The quality of the material may affect the ability of an optical sensor to generate signals in response to photons or thermal energy. Defects in the material used to detect photons may result in a recombination occurring quick enough such that a signal is not generated or the signal is not generated at a level that accurately reflects the presence of the carriers. This type of recombination is a Shockley-Read Hall (SRH) recombination, which is also referred to as a trap-assisted recombination.

These inconsistencies in the material may be, for example, a defect, a material impurity, or some other undesired inconsistency. This type of recombination is undesirable because a signal is not generated indicating the detection of a photon. As a result, the infrared detector device may not indicate as many detections of photons as desired.

As a result, signals may be generated that are not caused by the absorption of photons by the material. Consequently, the performance of an infrared detector device may suffer from this type of recombination.

The amount of Shockley-Read Hall recombination that occurs depends on the quality of the material. The quality of the material may vary between infrared detector devices and within an infrared detector device.

The variance of the quality of materials may result in an undesired quality in the images generated by an infrared focal plane array. For example, the inconsistencies in an infrared focal plane array may result in an undesired quality in a pixel or in hundreds of pixels depending on the size and location of the inconsistencies.

Inspections of the material for infrared focal plane arrays are performed. Defects in the material are often not readily identifiable, however, until the infrared focal plane array is fully fabricated and connected to circuits to read signals and generate images.

Testing at this stage of manufacturing for infrared focal plane arrays may be more expensive and time-consuming than desired. For example, if the images generated by an infrared focal plane array do not have a desired level of quality, the infrared focal plane array may be discarded. At this point, the cost and time to connect the circuits to the material has occurred. As a result, new circuits are needed, as well as another piece, or chip, of the material.

The large format of infrared focal plane arrays is very expensive and the production is generally of a low volume, such as 10 devices or less. Thus, it is desirable to know whether the quality of the material is suitable for use in an infrared focal plane array as soon as possible to avoid wasting resources on continuing manufacturing of an infrared focal plane array that has defects in the material for detecting photons.

Therefore, it would be desirable to have a method and apparatus that take into account at least some of the issues discussed above, as well as other possible issues. For example, it would be desirable to have a method and apparatus for inspecting materials at a time in manufacturing that overcome the technical problem of wasting resources and time that occurs when infrared detector devices are currently tested.

SUMMARY

Methods and apparatuses for identifying carrier lifetimes are disclosed herein. An embodiment of the present disclosure provides a method for identifying carrier lifetimes. A beam of light is sent to a group of locations on a material for an optical device. Photons emitted from the material are detected at each of the group of locations. A carrier lifetime is identified for each of the group of locations based on the photons detected from each of the group of locations.

Another embodiment of the present disclosure provides an apparatus comprising an inspection system. The inspection system sends a beam of light to a group of locations on a material for an optical device; detects photons emitted from the material at each of the group of locations; and identifies a carrier lifetime for each of the group of locations based on the photons detected from each of the group of locations.

Yet another embodiment of the present disclosure provides an inspection system comprising a test platform, a light source, a detector, and an analyzer. The test platform is configured to hold a material for an optical device. The light source sends a beam of light to a group of locations on the material held by the test platform. The detector detects photons emitted from the material at each of the group of locations in response to the beam of light being sent to the group of locations. The analyzer identifies a carrier lifetime for each of the group of locations based on the photons detected from each of the group of locations and a simulation of the photons emitted from the material at each of the group of locations.

Still another embodiment of the present disclosure provides a method for inspecting a material for an infrared detection device. The material for the infrared detection device is placed into an interior of a vessel. A vacuum is applied to the vessel. The material is cooled to a temperature at which the infrared detection device incorporating the material operates. A laser beam is sent through a window in the vessel onto the material in the vessel to form a spot for the laser beam on the material. The spot is moved to locations on the material. Photons emitted from the material are detected at each of the locations to which the spot moves. A carrier lifetime is identified for each of the locations based on the photons detected from each of the locations and a simulation of the photons emitted from the material at each of the locations.

The features and functions can be achieved independently in various embodiments of the present disclosure or may be combined in yet other embodiments in which further details can be seen with reference to the following description and drawings.

DETAILED DESCRIPTION

Figure 1:
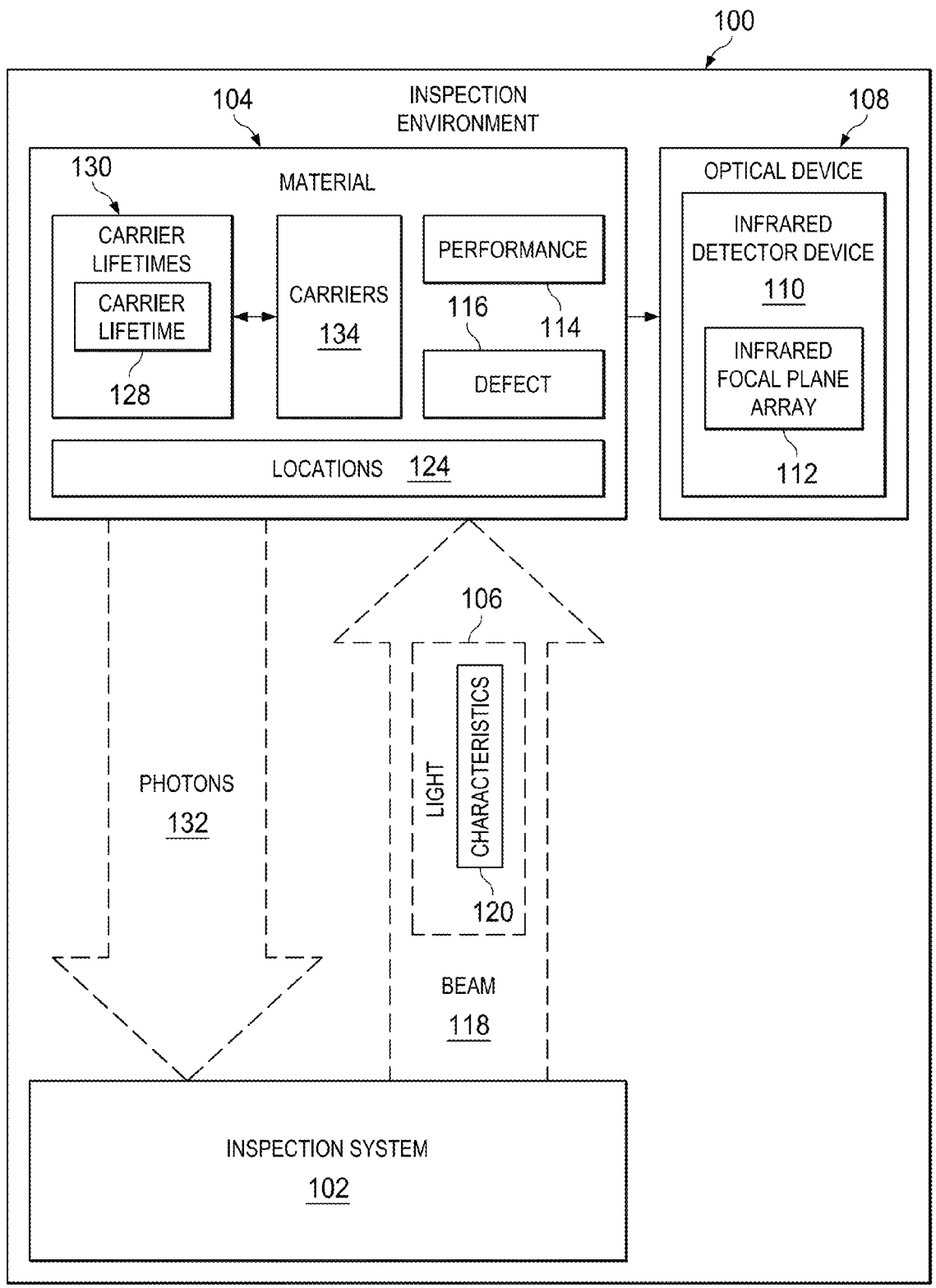
FIG. 1 is an illustration of a block diagram of an inspection environment in accordance with an illustrative embodiment.

The illustrative embodiments recognize and take into account one or more different considerations. For example, the illustrative embodiments recognize and take into account that testing a material that detects photons earlier during manufacturing may reduce the expense and time needed to manufacture infrared focal plane arrays or other infrared detector devices.

The illustrative embodiments recognize and take into account that inspecting a material that detects photons for an infrared detector device prior to attaching circuits to the material is desirable. If the material has undesired inconsistencies at a level that makes the material unsuitable for use in an infrared detector device, then the material layer may be discarded without discarding the circuits, and time taken to attach the circuits to the material and other manufacturing steps may be reduced or avoided.

The illustrative embodiments recognize and take into account that auger recombination and radiative recombination occur at rates that are intrinsic to the material being used for the detector. In other words, the rate at which these two types of recombination occur is only based on the material and not based on other factors. As a result, the lifetime of carriers based on these two types of recombination may be identified. These rates of recombination are referred to as recombination rates.

The illustrative embodiments also recognize and take into account that a trap-assisted recombination occurs from inconsistencies in the material. In other words, a trap-assisted recombination is not based on the properties of the material itself. For example, a trap-assisted recombination occurs when a defect is present in the material rather than some intrinsic property of the material.

The illustrative embodiments recognize and take into account that the carrier lifetime of the material as a whole depends on the carrier lifetimes of carriers as affected by these three types of recombination mechanisms. The illustrative embodiments recognize and take into account that the rates of auger recombination and radiative recombination do not vary for a particular material used in an optical device.

The illustrative embodiments recognize and take into account that the rate of recombination caused by trap-assisted recombination may vary at different locations in a material when defects are present. Thus, the illustrative embodiments recognize and take into account that the carrier lifetime for carriers that recombine from trap-assisted recombination may be the dominant contributor to the overall lifetime of carriers in the material.

The illustrative embodiments recognize and take into account that radiative recombination results in a photon being emitted from the material. The illustrative embodiments recognize and take into account that the emission of this photon may be used to inspect the material without connecting the material to circuits to generate signals from carriers.

For example, the illustrative embodiments recognize and take into account that when defects are absent in the material, trap-assisted recombination is substantially constant throughout the material. Consequently, the photons emitted from the material by radiative recombination are also substantially consistent.

When defects are present, the illustrative embodiments also recognize and take into account that trap-assisted recombination may be higher in areas where defects are located. As a result, the emission of photons in these locations may vary from other locations in the material where defects are not present.

Thus, the illustrative embodiments provide a method and apparatus for identifying carrier lifetimes in a material for an optical device. In one illustrative example, a method sends a beam of light to a group of locations on the material. Photons emitted from the material at each of the group of locations are detected. A carrier lifetime is identified for each of the group of locations based on the photons detected from each of the group of locations.

In this manner, the detection of carriers using circuits attached to a material is not needed to inspect the material. Instead, the photons emitted from the material may be used to identify carrier lifetimes for the material at different locations.

With reference now to the figures, and in particular, with reference to FIG. 1, an illustration of a block diagram of an inspection environment is depicted in accordance with an illustrative embodiment. Inspection environment 100 is an environment in which inspection system 102 may perform an inspection of material 104. In the illustrative example, material 104 is a material that generates a response to light 106. For example, material 104 may be a photosensitive material that has a bandgap. In the illustrative examples, the bandgap is a direct bandgap.

The bandgap is an energy range in the material where electron states cannot exist. The band gap represents the minimum energy difference between the top of the valence band and the bottom of the conduction band. The top of the valence band and the bottom of the conduction band, however, are not generally at the same value of the electron momentum. A direct band gap is present when the top of the valence band and the bottom of the conduction band occur at the same value of momentum.

This inspection of material 104 may be used to determine the suitability of material 104 for use in optical device 108. Optical device 108 is a hardware device that responds to light 106. For example, optical device 108 may be, for example, infrared detector device 110. More specifically, optical device 108 may be infrared focal plane array 112.

In an illustrative example, a number of different types of material may be used. For example, material 104 may be selected from one of mercury cadmium telluride (MCT), indium antimonide (InSb), indium arsenic antimonide (InAsSb), gallium indium arsenide (InGaAs), or some other suitable semiconductor that is sensitive to light 106 in the form of infrared light when optical device 108 is infrared detector device 110. As used herein, "a number of" when used with reference to items means one or more items. For example, a number of types of materials is one or more types of materials.

In this illustrative example, inspection system 102 performs an inspection of material 104 to determine whether performance 114 of material 104, in response to light 106, is suitable for use in optical device 108. Performance 114 may not be as high as desired when defect 116 is present in material 104. Defect 116 may be, for example, at least one of an impurity, a different element being present in material 104, a break, a crack, a void, an undesired lattice pattern, or some other inconsistency in material 104.

As used herein, the phrase "at least one of," when used with a list of items, means different combinations of one or more of the listed items may be used and only one of each item in the list may be needed. In other words, at least one of means any combination of items and number of items may be used from the list but not all of the items in the list are required. The item may be a particular object, thing, or a category.

For example, without limitation, "at least one of item A, item B, or item C" may include item A, item A and item B, or item B. This example also may include item A, item B, and item C or item B and item C. Of course, any combinations of these items may be present. In some illustrative examples, "at least one of" may be, for example, without limitation, two of item A; one of item B; and ten of item C; four of item B and seven of item C; or other suitable combinations.

In operation, inspection system 102 generates beam 118 of light 106 with a group of characteristics 120. As depicted, the number of characteristics 120 includes at least one of duration, intensity, spot size, wavelength, or other suitable characteristics for light 106.

During operation, inspection system 102 sends beam 118 of light 106 to a group of locations 124 on material 104. As used herein, "a group of", when used with respect to items, means one or more items. For example, a group of locations 124 is one or more of locations 124.

Inspection system 102 detects photons 132 emitted from material 104 at each of the group of locations 124. As depicted, inspection system 102 identifies carrier lifetime 128 for each of the group of locations 124 to form a group of carrier lifetimes 130 for material 104 based on photons 132 detected from each of the group of locations 124.

In the illustrative example, inspection system 102 detects photons 132 emitted from material 104 instead of detecting carriers 134 that may be formed in material 104 as part of inspecting material 104 for suitability for use in optical device 108. As a result, a circuit does not need to be connected to material 104 to inspect material 104 in identifying the presence of carriers 134 and carrier lifetimes 130.

Thus, in an illustrative example, inspection system 102 may be used to inspect material 104 at an earlier point in time as compared to currently used inspection techniques. Currently used techniques are employed to read signals after circuits are connected to the material. With inspection system 102, material 104 may be inspected without connecting a circuit to material 104.

As a result, the illustrative example provides a technical solution for inspecting materials at a time in manufacturing that overcomes the technical problem of wasting resources and time that occurs when infrared detector devices are currently tested. In this manner, a technical effect occurs in which the manufacturing of optical devices may occur at a lower cost, with less time, or both at a lower cost and with less time.

Figure 2:
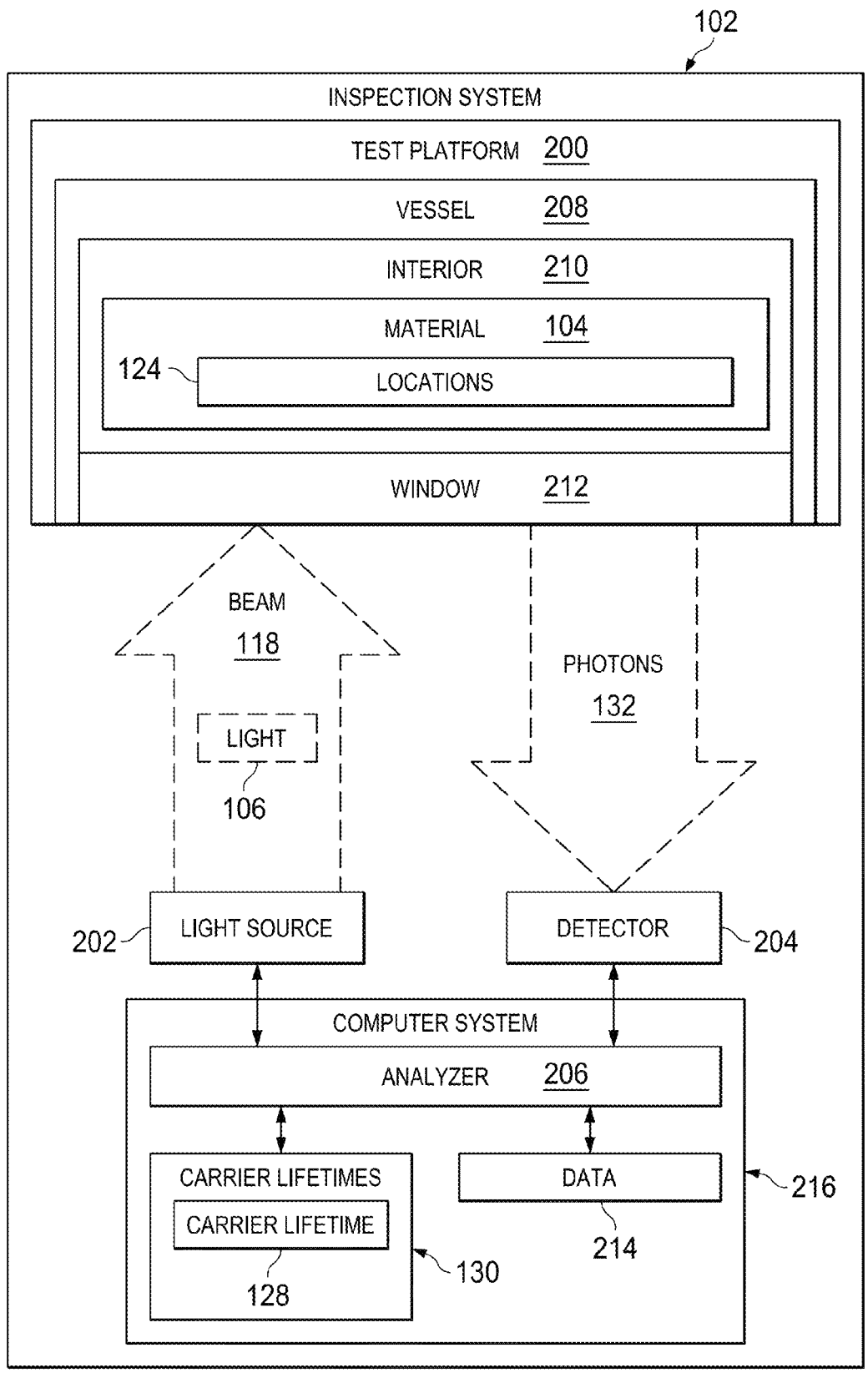
FIG. 2 is an illustration of a block diagram of an inspection system in accordance with an illustrative embodiment.

With reference next to FIG. 2, an illustration of a block diagram of an inspection system is depicted in accordance with an illustrative embodiment. An illustration of one implementation for inspection system 102 in FIG. 1 is shown. In the illustrative examples, the same reference numeral may be used in more than one figure. This reuse of a reference numeral in different figures represents the same element in the different figures.

In this illustrative example, inspection system 102 includes a number of different components. As depicted, inspection system 102 includes test platform 200, light source 202, detector 204, and analyzer 206.

Test platform 200 is a physical structure that holds material 104 for inspection in this illustrative example. For example, test platform 200 may be vessel 208. Material 104 may be placed into interior 210 of vessel 208 and held within interior 210 for inspection.

In the illustrative example, vessel 208 may take various forms. As depicted, vessel 208 may be selected from one of a vacuum flask, a Dewar flask, a thermos, a vacuum chamber, a pressurized chamber, or some other suitable structure.

As depicted, material 104, held by test platform 200, may be in various structures, part of various structures, or form various structures. For example, material 104 may be located in a structure selected from one of a wafer, a chip, an infrared detector device, an infrared focal plane array, or some other structure that is placed into interior 210 of vessel 208.

In the illustrative example, light source 202 is a hardware system that generates light 106 that is directed onto material 104. For example, light source 202 may include at least one of a light generator, optics, fiber-optic cables, or other suitable components for generating light 106 and directing light 106 onto material 104.

In this illustrative example, light source 202 generates light 106 with a group of characteristics 120 that is suitable to cause the generation of carriers 134 in material 104 and the emission of photons 132. For example, light source 202 may generate beam 118 of light 106 as a beam of coherent light. More specifically, beam 118 of light 106 may be a laser beam. Still more specifically, beam 118 of light 106 may be pulsed for a duration of time when light is sent to material 104.

Beam 118 of light 106 may be directed by light source 202 onto material 104 located in interior 210 of vessel 208 through window 212 in vessel 208. In this illustrative example, photons 132 are emitted from material 104 when beam 118 of light 106 is directed onto material 104.

Also, beam 118 of light 106 may be moved to locations 124 on material 104. The movement of beam 118 of light 106 from location to location in locations 124 results in photons 132 being emitted from location to location in locations 124.

As depicted, detector 204 is a hardware system that detects photons 132 emitted from locations 124 on material 104. Detector 204 may be implemented using at least one of an active pixel sensor, a charge coupled device (CCD), a cryogenic detector, a photoresistor, or other suitable devices.

Detector 204 generates data 214 from detecting photons 132. In this particular example, detector 204 sends data 214 to analyzer 206.

In the illustrative example, analyzer 206 identifies carrier lifetimes 130 for locations 124 based on data 214. In this manner, analyzer 206 identifies carrier lifetime 128 for each of the group of locations 124 based on photons 132 detected from each of the group of locations 124.

In this illustrative example, analyzer 206 also may control the operation of at least one of light source 202 or detector 204. Analyzer 206 may be implemented in software, hardware, firmware or a combination thereof. When software is used, the operations performed by analyzer 206 may be implemented in program code configured to run on hardware, such as a processor unit. When firmware is used, the operations performed by analyzer 206 may be implemented in program code and data and stored in persistent memory to run on a processor unit. When hardware is employed, the hardware may include circuits that operate to perform the operations in analyzer 206.

In the illustrative examples, the hardware may take the form of a circuit system, an integrated circuit, an application-specific integrated circuit (ASIC), a programmable logic device, or some other suitable type of hardware configured to perform a number of operations. With a programmable logic device, the device may be configured to perform the number of operations. The device may be reconfigured at a later time or may be permanently configured to perform the number of operations. Programmable logic devices include, for example, a programmable logic array, programmable array logic, a field programmable logic array, a field programmable gate array, and other suitable hardware devices. Additionally, the processes may be implemented in organic components integrated with inorganic components and may be comprised entirely of organic components excluding a human being. For example, the processes may be implemented as circuits in organic semiconductors.

In this illustrative example, analyzer 206 may be implemented in computer system 216. Computer system 216 is a hardware system that includes one or more data processing systems. When more than one data processing system is present, those data processing systems may be in communication with each other using a communications medium. The communications medium may be a network. The data processing systems may be selected from at least one of a computer, a server computer, a tablet, or some other suitable data processing system.

Figure 3:
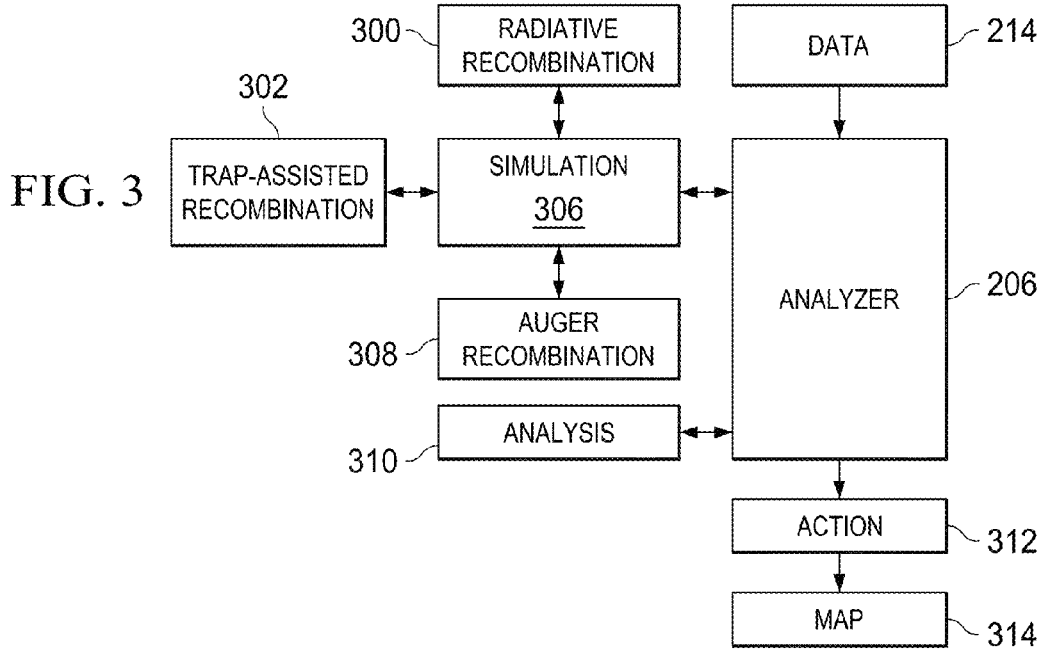
FIG. 3 is an illustration of a block diagram of a process for identifying carrier lifetimes in accordance with an illustrative embodiment.

With reference now to FIG. 3, an illustration of a block diagram of a process for identifying carrier lifetimes is depicted in accordance with an illustrative embodiment. In this illustrative example, analyzer 206 receives data 214 about photons 132 detected by detector 204.

In this illustrative example, analyzer 206 identifies carrier lifetime 128 for each of the group of locations 124 based on photons 132 detected from each of the group of locations 124. This identification takes into account that photons 132 are caused in part by recombination of carriers 134 in material 104 that occurs from radiative recombination 300. The part of photons 132 that occurs from radiative recombination is known as photoluminescence.

Radiative recombination 300 is substantially consistent for material 104. Defect 116 does not affect radiative recombination 300. The rate of radiative recombination 300 is based on the selection of material 104 and the concentration of carriers 134 in material 104 caused by beam 118 of light 106.

In this illustrative example, changes in photons 132 emitted by radiative recombination 300 may be affected by trap-assisted recombination 302. Trap-assisted recombination 302 may reduce radiative recombination 300. Additionally, trap-assisted recombination 302 may increase the dark currents present in material 104.

In this illustrative example, analyzer 206 identifies carrier lifetime 128 for each of the group of locations 124 based on data 214 about photons 132 emitted from material 104 and simulation 306 of photons 132 emitted from material 104 at each of the group of locations 124.

In this illustrative example, simulation 306 simulates recombinations of carriers 134 in material 104. Simulation 306 may simulate radiative recombination 300, trap-assisted recombination 302, and auger recombination 308.

In simulation 306, radiative recombination 300 and trap-assisted recombination 302 are assumed to be substantially the same material 104. As a result, the emission of photons 132 should not vary based on radiative recombination 300 and auger recombination 308. Changes in trap-assisted recombination 302 may result in changes in the numbers of photons 132 that are emitted from material 104.

As depicted in simulation 306, trap-assisted recombination 302 for material 104 is simulated in response to beam 118 of light 106 on material 104. As depicted, trap-assisted recombination 302 may be varied in simulation 306. This variation of trap-assisted recombination 302 is performed to find a level of trap-assisted recombination 302 that causes photons 132 emitted from material 104 in simulation 306 to match photons 132 as detected by detector 204 within a desired level of variance.

The desired level of variance is how much difference between photons 132 being simulated and photons 132 as detected is acceptable for simulating the emission of photons 132 in simulation 306 versus the emission of photons 132 detected by detector 204. The desired level of variance may be based on some level of acceptable error.

Analyzer 206 identifies carrier lifetime 128 for each of the group of locations 124 to form a group of carrier lifetimes 130 for the group of locations 124 based on trap-assisted recombination 302 identified that causes emission of photons 132 and simulation 306 to match photons 132 detected by detector 204 with a desired level of variance. In the illustrative example, analyzer 206 may perform analysis 310 based on photons 132 detected by detector 204 and photons 132 in simulation 306. The analysis may be based on varying the amount of trap-assisted recombination 302.

As depicted, analyzer 206 may perform action 312 based on analysis 310. Action 312 may take a number of different forms. In one illustrative example, action 312 includes generating map 314. Map 314 may be a map of carrier lifetimes 130 in material 104.

Map 314 may be used to perform other actions. For example, map 314 may be used to identify portions of material 104 that may be used for optical devices. For example, map 314 may indicate that one portion of material 104 may be suitable for use in an optical device while another portion of material 104 is unsuitable for use in an optical device.

As another example, map 314 may be used as a guide to show what parts of material 104 should be used. For example, map 314 may show how material 104 may be diced when material 104 is in a wafer. The dicing of material 104 may be in a manner that leaves portions of material 104 for other suitable uses in optical devices. The other portions of material 104 may be discarded or recycled.

In another illustrative example, action 312 may take other forms in addition to or including generating map 314. For example, action 312 may include at least one of sending a message, generating an alert, recommending discarding material 104 in the case that material 104 is not suitable for use, or other suitable actions.

As a result, computer system 216 in FIG. 2 operates as a special purpose computer system in which analyzer 206 in computer system 216 enables identifying carrier lifetimes 130 in material 104 in various ones of locations 124. In particular, analyzer 206 transforms computer system 216 into a special purpose computer system as compared to currently available general computer systems that do not have analyzer 206.

Computer system 216 performs a transformation of data 214. For example, analyzer 206 in computer system 216 uses the number of photons detected in data 214 to identify the carrier lifetime for trap-assisted recombination 302 by comparing photons 132 detected with photons that would be emitted in a simulation of trap-assisted recombination 302 for the material such that the data has a different function or has a different use.

Figure 4:
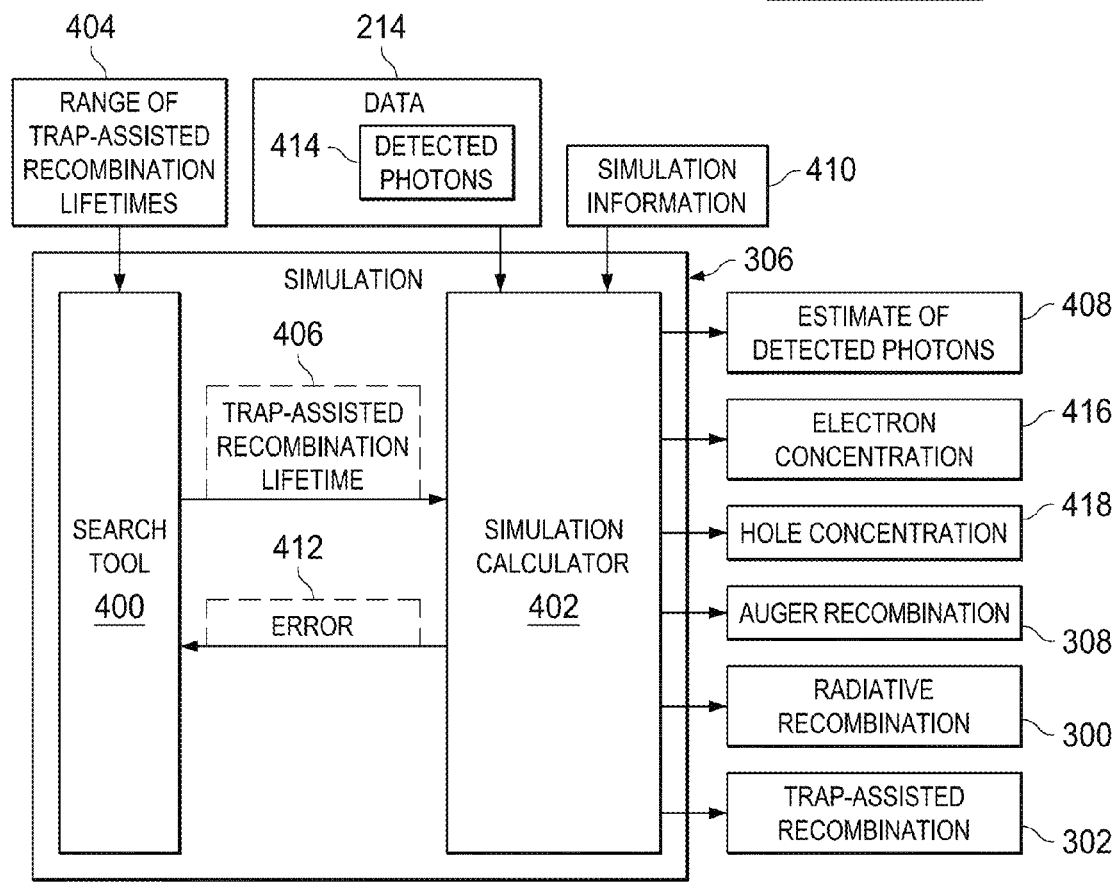
FIG. 4 is an illustration of a block diagram of data flow simulating trap-assisted recombination for a material in accordance with an illustrative embodiment.

Turning to FIG. 4, an illustration of a block diagram of data flow simulating trap-assisted recombination for a material is depicted in accordance with an illustrative embodiment. In this figure, an example of data flow of a process used to identify trap-assisted recombination 302 for material 104 through simulation 306 is shown. In this illustrative example, simulation 306 includes search tool 400 and simulation calculator 402.

Search tool 400 identifies trap-assisted recombination 302 for material 104 by searching for a solution to a variable that reduces an amount of error to a desired level. As depicted, the error is between an estimate of detected photons based on the variable and actual detected photons from material 104.

In this illustrative example, the variable is range of trap-assisted recombination lifetimes 404. Range of trap-assisted recombination lifetimes 404 is a range of values of trap-assisted recombination lifetimes for material 104. Trap-assisted recombination lifetime 406 is the average carrier lifetime in material 104 before trap-assisted recombination occurs.

As depicted, search tool 400 generates trap-assisted recombination lifetime 406 based on the range of trap-assisted recombination lifetimes 404. Search tool 400 sends trap-assisted recombination lifetime 406 to simulation calculator 402.

Simulation calculator 402 identifies estimate of detected photons 408 based on trap-assisted recombination lifetime 406 received from search tool 400 and simulation information 410. Simulation calculator 402 then identifies error 412 based the difference between estimate of detected photons 408 and detected photons 414 in data 214. Detected photons 414 is data about photons 132 emitted from material 104.

Simulation calculator 402 sends error 412 to search tool 400. The process illustrated in FIG. 4 is repeated until search tool 400 finds the trap-assisted recombination lifetime in range of trap-assisted recombination lifetimes 404 for which error 412 is closest to zero. In other words, search tool 400 identifies the trap-assisted recombination lifetime in range of trap-assisted recombination lifetimes 404 for which the estimate of detected photons 408 is closest to detected photons 414.

As depicted, simulation calculator 402 also generates electron concentration 416, hole concentration 418, auger recombination 308, radiative recombination 300, and trap-assisted recombination 302 based on simulation information 410 and trap-assisted recombination lifetime 406. Electron concentration 416 is the number of electrons per unit volume at a selected temperature in the absence of photon absorption. Hole concentration 418 is the number of electron-holes per unit volume at a selected temperature in the absence of photon absorption.

Figure 5:
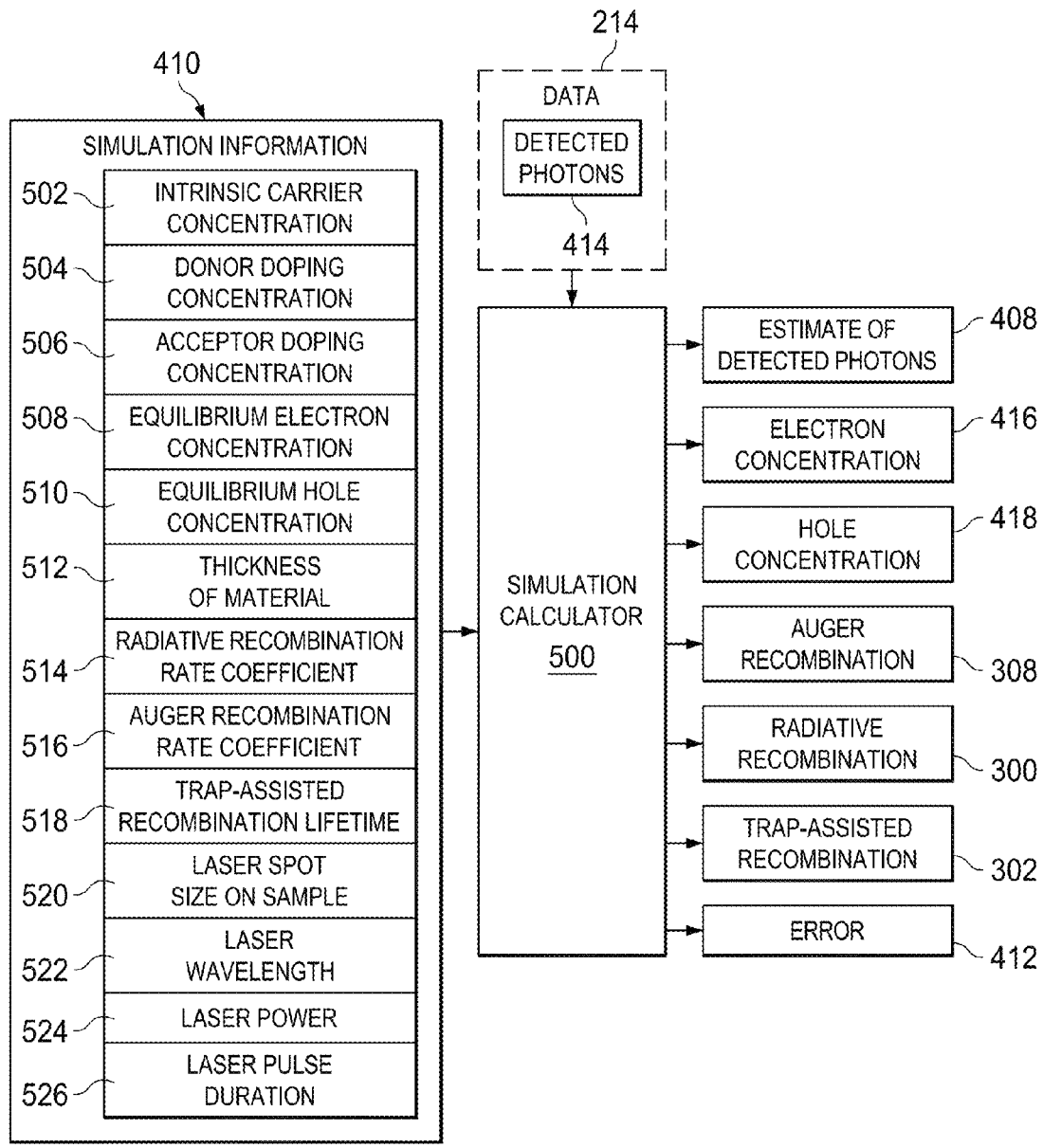
FIG. 5 is an illustration of a block diagram of data flow for generating an estimate of error for trap-assisted recombination for a material in accordance with an illustrative embodiment.

Turning next to FIG. 5, an illustration of a block diagram of data flow for generating an estimate of error for trap-assisted recombination for a material is depicted in accordance with an illustrative embodiment. In this figure, an example of data flow used to identify error 412 based on the difference between estimate of detected photons 408 and detected photons 414 is shown. Simulation calculator 500 in FIG. 5 is an example of simulation calculator 402 in FIG. 4.

In this example, simulation calculator 500 uses simulation information 410 in generating error 412. In this example, simulation information 410 is provided by a human operator. The types of information in simulation information 410 include intrinsic carrier concentration 502, donor doping concentration 504, acceptor doping concentration 506, equilibrium electron concentration 508, equilibrium hole concentration 510, thickness of material 512, radiative recombination rate coefficient 514, auger recombination rate coefficients 516, trap-assisted recombination lifetime 518, laser spot size on sample 520, laser wavelength 522, laser power 524, and laser pulse duration 526.

In this example, intrinsic carrier concentration 502 is the number of electrons and electron-holes per unit volume which are free of defects in material 104. These defects are examples of defect 116 in FIG. 1.

Donor doping concentration 504 is the number of atoms per unit volume placed in material 104 that provide an excess electron. An excess electron is an electron without a corresponding electron-hole.

As depicted, acceptor doping concentration 506 is the number of atoms per unit volume placed in material 104 that provides an excess electron-hole. An excess electron-hole is an electron-hole without a corresponding electron.

Equilibrium electron concentration 508 is the number of electrons per unit volume at a given temperature in the absence of photon absorption. Equilibrium hole concentration 510 is the number of electron-holes per unit volume at a given temperature in the absence of photon absorption.

Radiative recombination rate coefficient 514 is a value used to indicate the rate of radiative recombination for the concentration of electrons and electron-holes in material 104. Auger recombination rate coefficients 516 are values used to indicate the rate of auger recombination for the concentration of electrons and electron-holes in material 104.

In this illustrative example, trap-assisted recombination lifetime 518 is an estimate of the rate of trap-assisted recombination for the concentration of electrons and electron-holes in material 104. For example, trap-assisted recombination lifetime 518 may be used by search tool 400 in FIG. 4 as trap-assisted recombination lifetime 406.

Laser spot size on sample 520 is the size of beam 118 of light 106 on material 104. The size is described as a diameter or radius if the laser spot is circular in the illustrative example.

As depicted, laser wavelength 522 is the wavelength of beam 118 of light 106. Laser power 524 is the power of beam 118 of light 106. Laser pulse duration 526 is the amount of time beam 118 of light 106 is sent to material 104.

In this figure, simulation calculator 500 identifies trap-assisted recombination lifetime 518 in simulation information 410. Trap-assisted recombination lifetime 518 may be an estimate.

Simulation calculator 500 identifies error 412 based on the difference between estimate of detected photons 408 and detected photons 414 in data 214. Simulation calculator 500 identifies estimate of detected photons 408 using the following equations:

$$n(t+\Delta t)=n(t)+\Delta t G_{optical}(t)-\Delta t(U_{aug}+U_{rad}+U_{SRH}) \quad (1)$$

$$p(t+\Delta t)=p(t)+\Delta t G_{optical}(t)-\Delta t(U_{aug}+U_{rad}+U_{SRH}) \quad (2)$$

where equations (1) and (2) are used to determine the carrier concentration of both electrons n and holes p after a time step $\Delta t$; $G_{optical}(t)$ is the optical carrier generation rate; and $U_{aug}$, $U_{rad}$, and $U_{SRH}$ are the net recombination rates respectfully from auger, radiative, and trap-assisted recombination.

These recombination rates are identified using the following equations:

$$U_{aug} = C_n(n^2 p - n_0^2 p_0) + C_p(np^2 - n_0 p_0^2) \quad (3)$$

$$U_{rad} = B(np - n_i^2) \quad (4)$$

$$U_{SRH} = \frac{(np - n_i^2)}{\tau_{SRH-n}(p + p_1) + \tau_{SRH-p}(n + n_1)} \quad (4)$$

$$n_0 p_0 = n_i^2 \quad (5)$$

where $n_0$ and $p_0$ are the equilibrium concentrations of electrons and holes, and $n_1$ is the intrinsic carrier concentration; $n_1$ and $p_1$ are the trap-assisted recombination densities which are set equal to $n_0$ and $p_0$ when lack of knowledge about the nature of the defect states is present; and $\tau_{SRH-n}$ and $\tau_{SRH-p}$ are the trap-assisted recombination lifetimes for electrons and holes, which are set equal to each other and regarded as the primary variables of interest.

Simulation calculator 500 identifies recombination rate coefficients using the following equations:

$$B = 5.8 \times 10^{-13} \sqrt{\varepsilon_\infty} \left(\frac{m_0}{m_c^* + m_v^*}\right)^{\frac{3}{2}} \left(1 + \frac{m_0}{m_c^*} + \frac{m_0}{m_v^*}\right) \times \left(\frac{300}{T}\right)^{\frac{3}{2}} (E_g^2 + 3kTE_g + 2.75k^2T^2) \quad (6)$$

$$C_n = \frac{\left(\frac{m_c^*}{m_0}\right)|F_1 F_2|^2}{2n_i^2(3.8 \times 10^{-18})\varepsilon_\infty^2 \left(1 + \frac{m_c^*}{m_v^*}\right)^{\frac{1}{2}} \left(1 + \frac{2m_c^*}{m_v^*}\right) \times \left(\frac{E_g}{kT}\right)^{\frac{-3}{2}} \exp\left(-\frac{1 + \frac{2m_c^*}{m_v^*}}{1 + \frac{m_c^*}{m_v^*}} \frac{E_g}{kT}\right)} \quad (7)$$

$$C_p = C_n \left[\frac{1 - \frac{3E_g}{kT}}{6\left(1 - \frac{5E_g}{4kT}\right)}\right] \quad (8)$$

where B, $C_n$, and $C_p$ are recombination rate coefficients; $m_0$ is the mass of an electron, and $m^*_c$ and $m^*_v$ are the effective masses of electrons and holes in the conduction and valence bands; and $|F_1 F_2|$ is the overlap integral of the Bloch functions, and its value is 0.2 in these simulations because the actual value is not precisely known.

As an example for the common infrared detector material mercury cadmium telluride (MCT), simulation calculator 500 identifies intrinsic carrier concentration $n_i$ and band gap $E_g$ for MCT as a function of temperature T and composition x as found in the material $Hg_{(1-x)}Cd_xTe$. Simulation calculator 500 identifies intrinsic carrier concentration $n_i$ and band gap $E_g$ for MCT using the following equations:

$$E_g = -0.302 + 1.93x + 5.35 \times 10^{-4} T(1-2x) - 0.81x^2 + 0.832x^3 \quad (9)$$

$$n_i = (5.585 - 3.82x + 1.753 \times 10^{-3} T - 1.364 \times 10^{-3} xT) \times \quad (10)$$
$$10^{14} E_g^{\frac{3}{4}} T^{\frac{3}{2}} \exp\left(\frac{-E_g}{2kT}\right)$$

Simulation calculator 500 further identifies equilibrium carrier concentrations using the following equations:

$$n_0 = \frac{N_D - N_A}{2} + \sqrt{\left(\frac{N_D - N_A}{2}\right)^2 + n_i^2} \quad (11)$$

$$p_0 = \frac{N_A - N_D}{2} + \sqrt{\left(\frac{N_A - N_D}{2}\right)^2 + n_i^2} \quad (12)$$

where $N_D$ and $N_A$ are the donor and acceptor doping concentrations.

The illustration of inspection environment 100 and the different components in inspection environment 100 in FIGS. 1-5 are not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, inspection system 102 may include one or more test platforms in addition to or in place of test platform 200 in FIG. 2. Additional detectors may be used with these test platforms. Further, light source 202 may be a single light generator with optics for fiber-optic cables to correct light 106 to other materials in addition to material 104 that may be located in the different test platforms.

Figure 6:
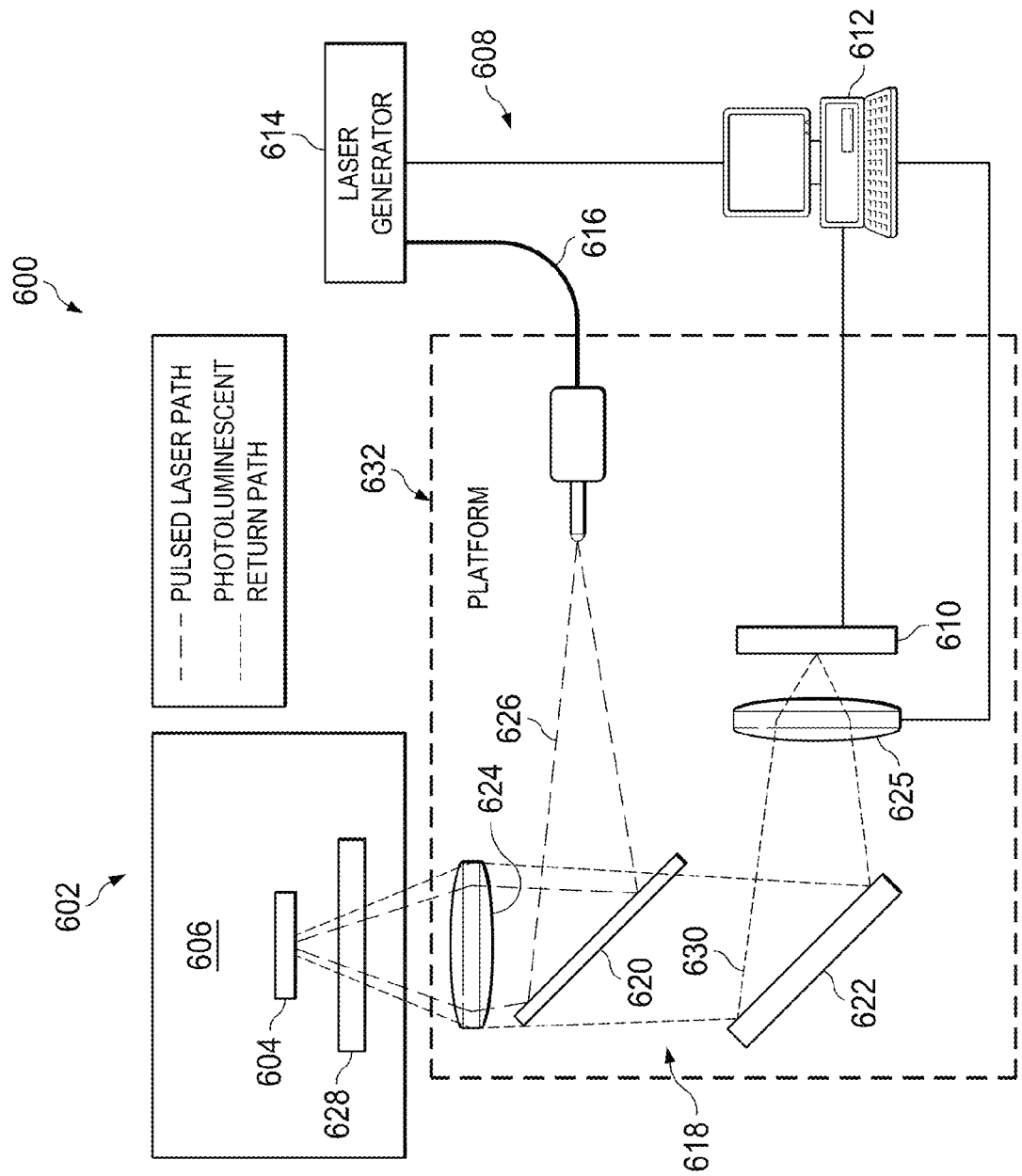
FIG. 6 is an illustration of an inspection environment in accordance with an illustrative embodiment.

With reference now to FIG. 6, an illustration of an inspection environment is depicted in accordance with an illustrative embodiment. In this depicted example, inspection environment 600 is an example of one implementation for inspection environment 100 shown in block form in FIG. 1.

Inspection system 602 in inspection environment 600 performs an inspection of test sample 604. Test sample 604 is a material that has a direct bandgap that is intended for use in an infrared detector device, such as an infrared focal plane array.

In this illustrative example, inspection system 602 includes a number of different components. As depicted, inspection system 602 includes Dewar flask 606, pulsed laser system 608, fast detector 610, and computer 612.

As depicted, Dewar flask 606 is an example of an implementation for test platform 200 in FIG. 2. Fast detector 610 is an example of an implementation for detector 204 in FIG. 2.

As depicted, pulsed laser system 608 is an example of light source 202 in FIG. 2. Computer 612 is an example of analyzer 206 in FIG. 2.

In this illustrative example, Dewar flask 606 is a structure in which test sample 604 may be placed for inspection. In this illustrative example, a vacuum may be drawn within Dewar flask 606. Additionally, the temperature may be lowered to a cryogenic temperature within Dewar flask 606. This cryogenic temperature is the temperature at which an infrared detection device operates.

Pulsed laser system 608 includes a number of components. As depicted, pulsed laser system 608 includes laser generator 614, optical fiber 616, and optics 618.

Laser generator 614 generates a laser beam that is pulsed. This pulsed laser beam may be directed through optical fiber 616 to optics 618. In this illustrative example, optics 618 includes a number of different components. As depicted, optics 618 includes beam splitter 620, mirror 622, lens 624, and lens 625.

Pulsed laser path 626 is sent from optical fiber 616 to test sample 604 located in Dewar flask 606. Part of pulsed laser path 626 is defined by beam splitter 620 and lens 624. Pulsed laser path 626 goes into Dewar flask 606 through window 628 in Dewar flask 606.

In response to the laser beam following pulsed laser path 626, photons are emitted from test sample 604. These photons follow return path 630. Return path 630 goes from test sample 604 to fast detector 610. Return path 630 passes through window 628 and passes through beam splitter 620. Return path 630 then goes to fast detector 610 via mirror 622 and through lens 625.

In this illustrative example, fast detector 610 is a detector with a response time that is shorter than the carrier lifetime of test sample 604. Fast detector 610 generates data in response to detecting the photons reaching fast detector 610 along return path 630 for the route. The data is sent to computer 612.

In this illustrative example, computer 612 analyzes the data. Additionally, computer 612 also controls the operation of pulsed laser system 608 and fast detector 610.

In this illustrative example, optics 618 and optical fiber 616 are associated with platform 632. When one component is "associated" with another component, the association is a physical association in the depicted examples. For example, a first component, optics 618 or optical fiber 616, may be considered to be physically associated with a second component, platform 632, by at least one of being secured to the second component, bonded to the second component, mounted to the second component, welded to the second component, fastened to the second component, or connected to the second component in some other suitable manner. The first component also may be connected to the second component using a third component. The first component may also be considered to be physically associated with the second component by being formed as a part of the second component, an extension of the second component, or both.

As depicted, platform 632 is a physical structure that is configured to move about a number of axes. For example, platform 632 may allow for 6 degrees of freedom in positioning and moving pulsed laser path 626 with respect to test sample 604. More particularly, pulsed laser path 626 may be positioned and moved along three perpendicular axes of three-dimensional space and rotated about the three perpendicular axes with respect to test sample 604. This movement may allow for directing a pulsed laser beam to different locations on test sample 604. In the illustrative example, platform 632 may be, for example, a housing, a frame, or some other suitable type of structure.

The illustration of inspection environment 600 in FIG. 6 is only meant as an example of one implementation for inspection environment 100 shown in block form in FIG. 1. The illustration of inspection environment 600 is not meant to limit the manner in which other illustrative examples may be implemented.

For example, Dewar flask 606 may be moved in place of or in addition to the movement of platform 632. As another example, pulsed laser system 608 may include one or more other optical fibers in addition to optical fiber 616. As a result, multiple laser beams may be directed towards one or more samples that may be located in Dewar flask 606 for other test platforms that may be used in place of or in addition to Dewar flask 606.

As another example, pulsed laser system 608 may include an oscilloscope that reads the data from fast detector 610. In this example, the oscilloscope sends the data to computer 612.

Figure 7:
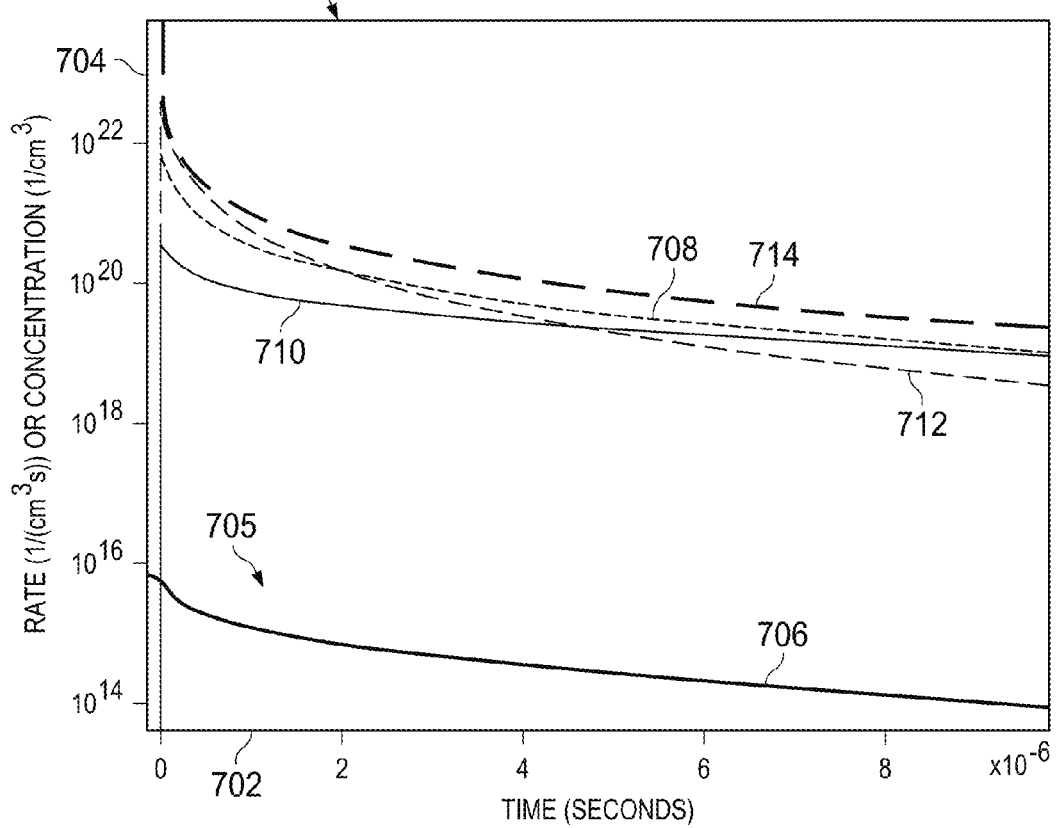
FIG. 7 is an illustration of a graph of recombination rates from a simulation in accordance with an illustrative embodiment.

With reference next to FIG. 7, an illustration of a graph of recombination rates from a simulation is depicted in accordance with an illustrative embodiment. In this illustration, graph 700 shows output from simulation 306. In graph 700, x-axis 702 is time in seconds, and y axis 704 is the rates of recombination or hole concentration in centimeters$^{-3}$. As depicted, the lines shown on graph 700 represent recombination rates for different types of recombination for material 104 and hole concentration rate 705 for material 104.

In the illustrative example, line 706 shows hole concentration rate 705. Hole concentration rate 705 in line 706 is based on hole concentration 418. The types of recombination rates for material 104 shown in graph 700 include radiative recombination rate 708, trap-assisted recombination rate 710, auger recombination rate 712, and total recombination rate 714.

As depicted, radiative recombination rate 708 is based on radiative recombination 300; trap-assisted recombination rate 710 is based on trap-assisted recombination 302; and auger recombination rate 712 is based on auger recombination 308. Recombination rates are based on recombination lifetimes. Total recombination lifetime is based on the following equation:

$$\frac{1}{\tau_{total}} = \frac{1}{\tau_{rad}} + \frac{1}{\tau_{SRH}} + \frac{1}{\tau_{aug}} \quad (14)$$

where $\tau_{total}$ total recombination lifetime, $\tau_{rad}$ is radiative recombination lifetime, $\tau_{SRH}$ is trap-assisted recombination lifetime, and $\tau_{aug}$ is auger recombination lifetime.

Figure 8:
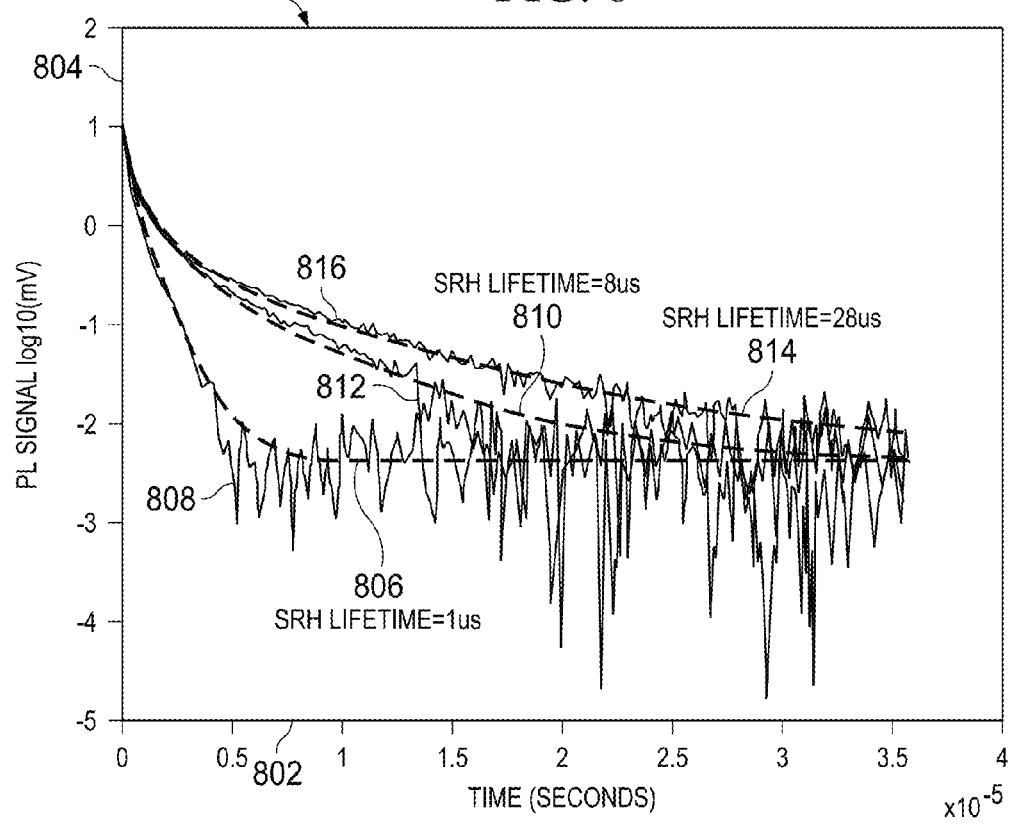
FIG. 8 is an illustration of a graph of photons detected and the simulated estimate of detected photons for different carrier lifetimes in accordance with an illustrative embodiment.

Turning to FIG. 8, an illustration of a graph of photons detected and the simulated estimate of detected photons for different carrier lifetimes is depicted in accordance with an illustrative embodiment. As depicted in graph 800, carrier lifetimes from a simulation and data generated from the detection of photons are shown.

In this illustration, graph 800 shows examples of the trap-assisted recombination lifetimes identified by simulation 306 in FIG. 4 for different locations on material 104. In graph 800, x-axis 802 is time in seconds, and y axis 804 is detection of photons in millivolts on a logarithmic scale.

As depicted, line 806 shows an estimate of detected photons for a trap-assisted lifetime of 1 µs. Trap-assisted lifetime in line 806 is identified by simulation 306 based on detected photons 808; trap-assisted lifetime in line 810 is identified by simulation 306 based on detected photons 812; and trap-assisted lifetime in line 814 is identified by simulation 306 based on detected photons 816. These detected photons are examples of detected photons 414 for three different locations of material 104. These trap-assisted recombination lifetimes are the trap-assisted recombination lifetimes for which error 412 is closest to zero for the different locations.

Figure 9:
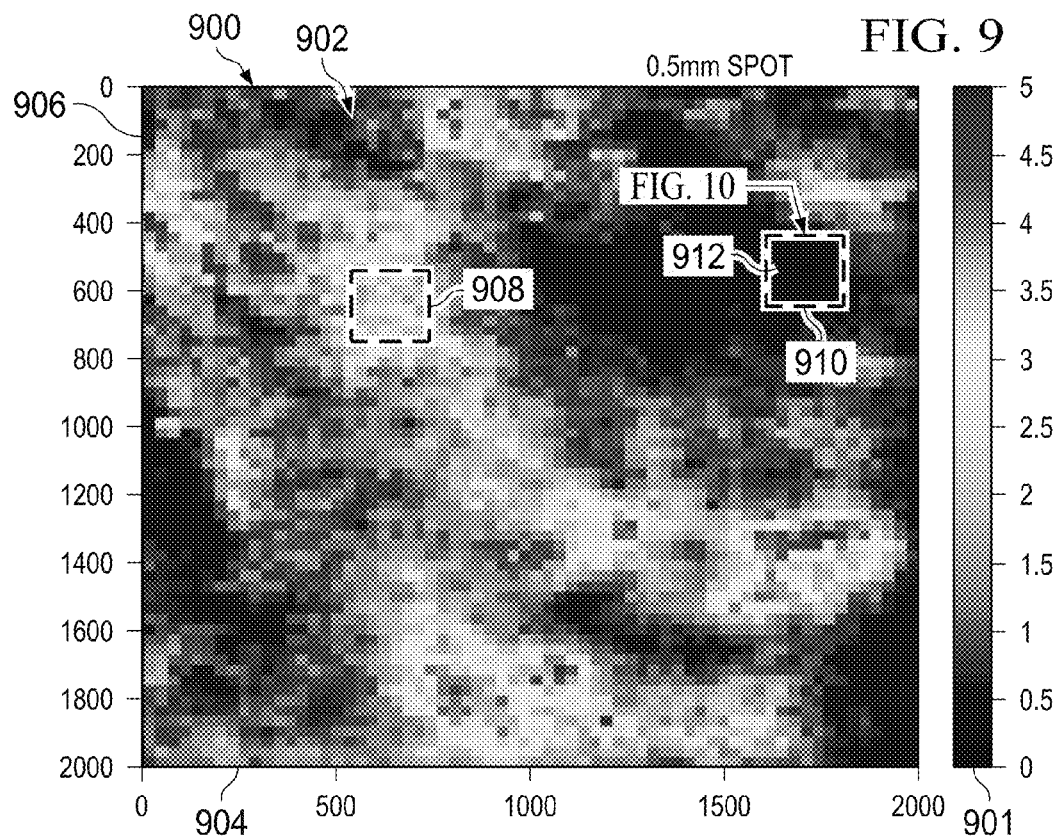
FIG. 9 is an illustration of a map representing trap-assisted recombination lifetimes for a material in accordance with an illustrative embodiment.

Turning now to FIG. 9, an illustration of a map representing trap-assisted recombination lifetimes for a material is depicted in accordance with an illustrative embodiment. In FIG. 9, map 900 is an example of one form of map 314 in FIG. 3. As depicted, map 900 is an image of a material that has been inspected.

In this illustrative example, scale 901 is a legend for the trap-assisted recombination lifetimes in microseconds shown on map 900. Locations 902 on map 900 are identified by x-axis 904 and y-axis 906 of map 900. Map 900 shows different trap-assisted lifetimes in different regions. For example, region 908 shows trap-assisted recombination lifetimes that are longer than region 910 and may be more suitable for use in an infrared detector device. As another example, region 910 shows trap-assisted recombination lifetimes that may not be suitable for use in infrared detector devices. A defect is present in region 910 in this example.

In this illustrative example, a 0.5 mm laser spot size was used to identify the trap-assisted recombination lifetimes shown on map 900 for material 104. As depicted, defect 912 in material 104 is in region 910.

Figure 10:
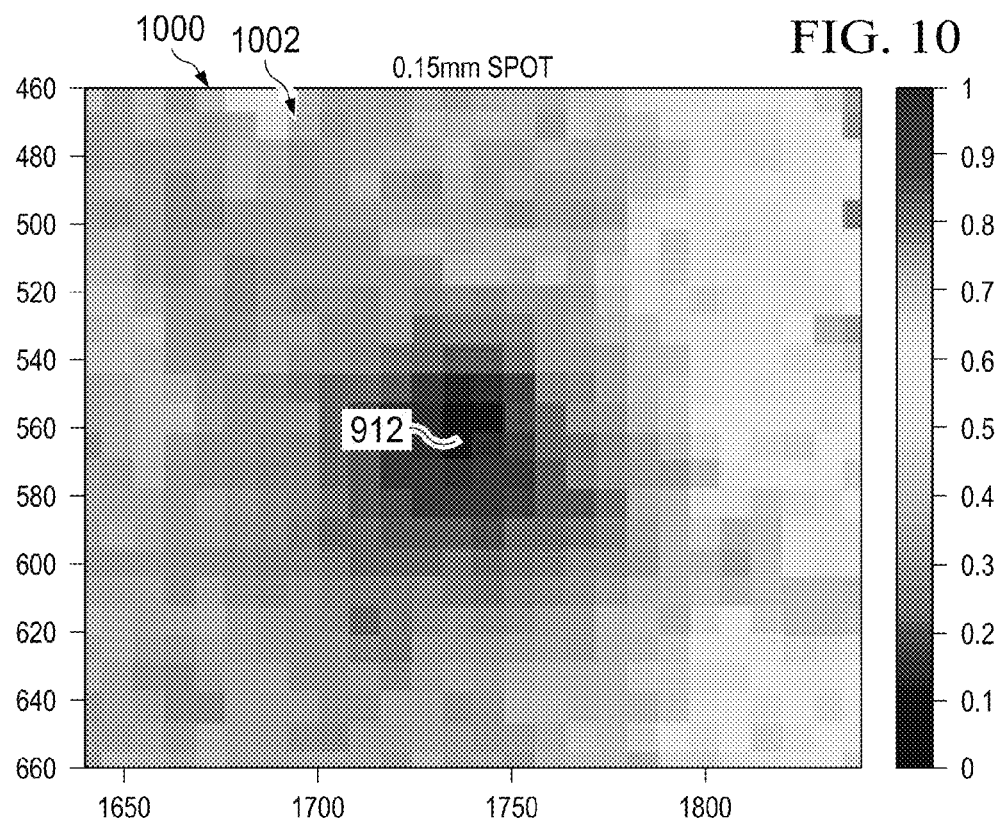
FIG. 10 is an illustration of a map having a higher resolution in accordance with an illustrative embodiment.

With reference next FIG. 10, an illustration of a map having a higher resolution is depicted in accordance with an illustrative embodiment. In this illustration, map 1000 shows locations 1002 that represent additional trap-assisted recombination lifetimes identified by simulation 306 for material 104. Map 1000 is a higher resolution map of region 910 in FIG. 9. In this illustrative example, a 0.15 mm laser spot size was used to identify the trap-assisted recombination lifetimes of material 104 for region 910 having defect 912.

Figure 11:
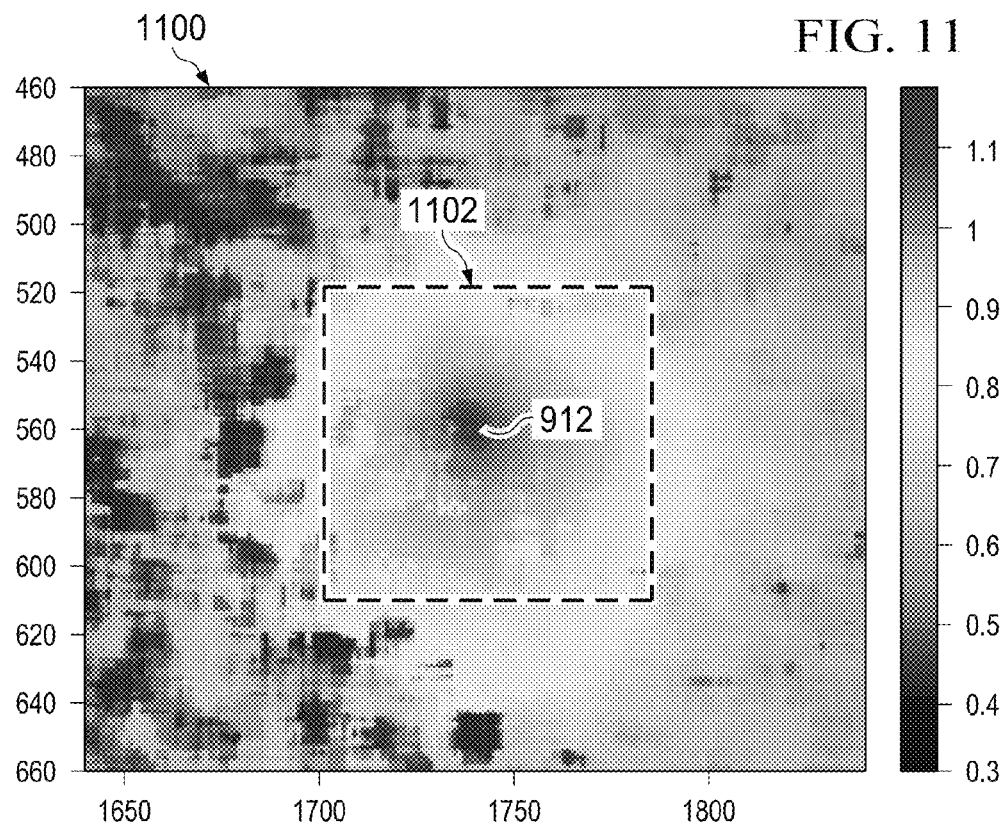
FIG. 11 is an illustration of a map generated from reading signals from an infrared focal plane array in accordance with an illustrative embodiment.

With reference now to FIG. 11, an illustration of a map generated from reading signals from an infrared focal plane array is depicted in accordance with an illustrative embodiment. In this illustration, map 1100 is an infrared image generated by an infrared focal plane array. The infrared focal plane array in this example is formed using region 910 of material 104. As depicted, section 1102 of map 1100 shows defect 912 in material 104.

Figure 12:
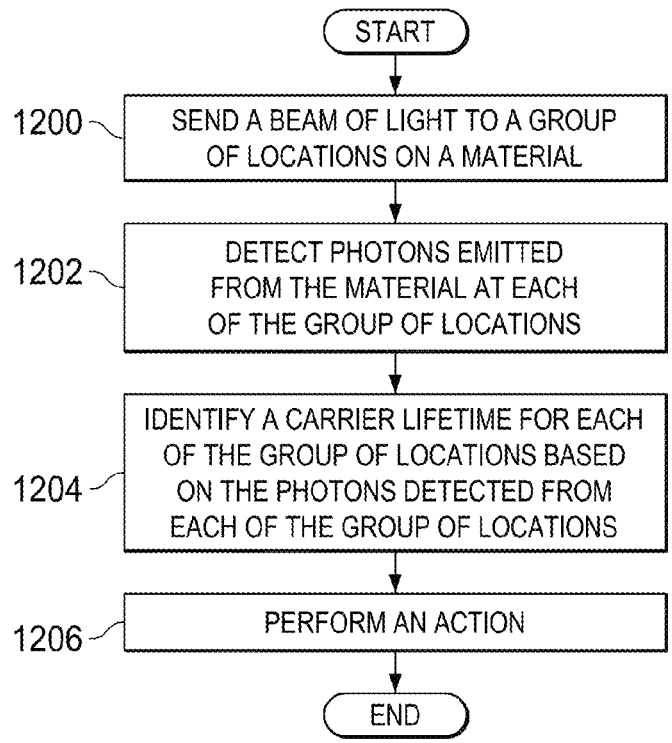
FIG. 12 is an illustration of a flowchart of a process for identifying carrier lifetimes in a material for use in an optical device in accordance with an illustrative embodiment.

Turning next to FIG. 12, an illustration of a flowchart of a process for identifying carrier lifetimes in a material for use in an optical device is depicted in accordance with an illustrative embodiment. The process illustrated in FIG. 12 may be implemented in inspection environment 100 in FIG. 1. In particular, the process may be implemented in inspection system 102 to inspect material 104 and identify carrier lifetimes 130 to determine suitability of material 104 for use in optical device 108.

The process begins by sending a beam of light to a group of locations on the material (step 1200). The process then detects photons emitted from the material at each of the group of locations (step 1202).

Next, the process identifies a carrier lifetime for each of the group of locations based on the photons detected from each of the group of locations (step 1204). The process then performs an action (step 1206) with the process terminating thereafter.

Figure 13:
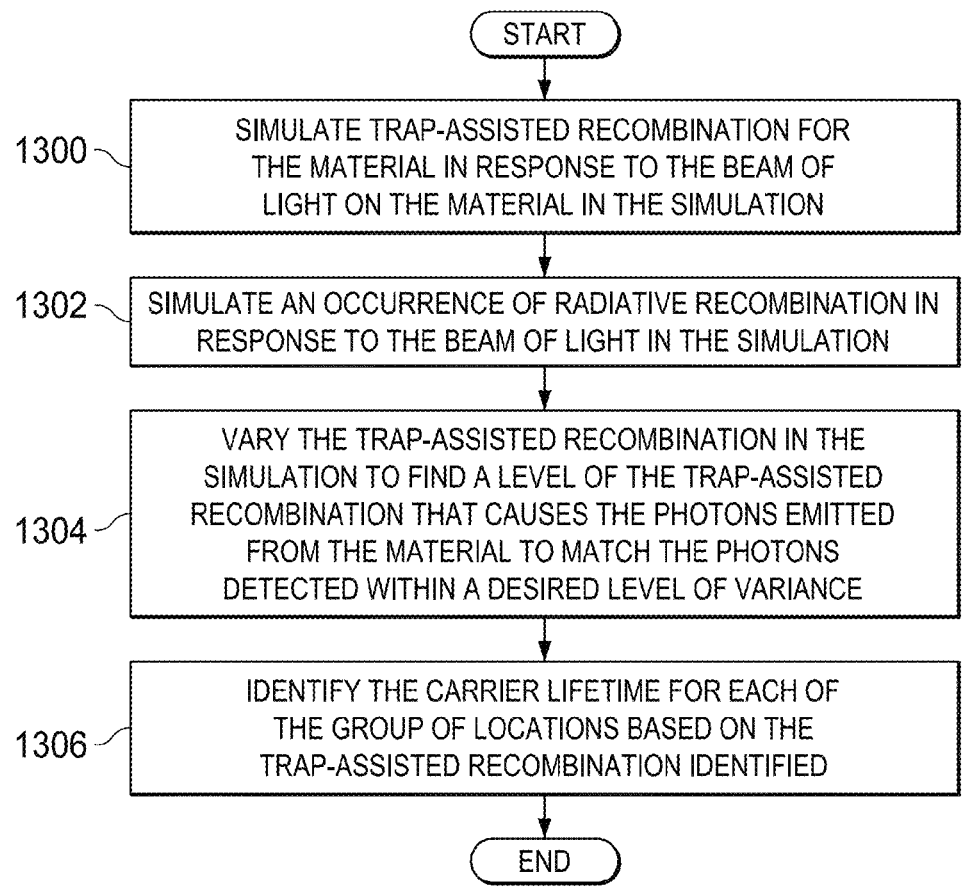
FIG. 13 is an illustration of a flowchart of a process for identifying carrier lifetimes in accordance with an illustrative embodiment.

With reference now to FIG. 13, an illustration of a flowchart of a process for identifying carrier lifetimes is depicted in accordance with an illustrative embodiment. The process illustrated in FIG. 13 is an example of one implementation for step 1204 in FIG. 12.

The process begins by simulating trap-assisted recombination for the material in response to the beam of light on the material in the simulation (step 1300). The process also simulates an occurrence of radiative recombination in response to the beam of light in the simulation (step 1302).

The process varies the trap-assisted recombination in the simulation to find a level of the trap-assisted recombination that causes the photons emitted from the material to match the photons detected within a desired level of variance (step 1304). The process identifies the carrier lifetime for each of the group of locations based on the trap-assisted recombination identified (step 1306) with the process terminating thereafter.

Figure 14:
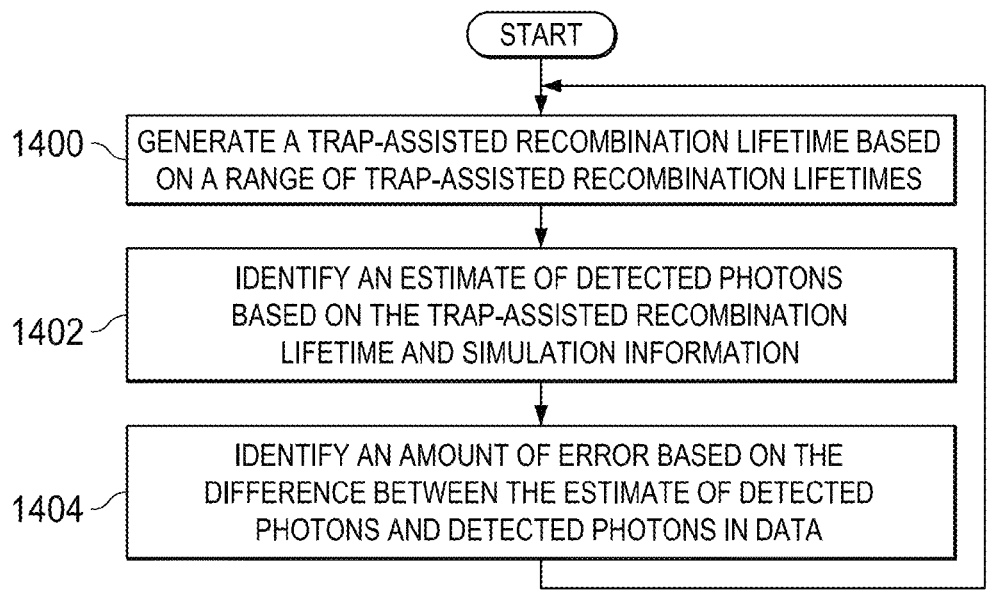
FIG. 14 is an illustration of a flowchart of a process for identifying trap-assisted recombination lifetimes in accordance with an illustrative embodiment.

Turning to FIG. 14, an illustration of a flowchart of a process for identifying trap-assisted recombination lifetimes is depicted in accordance with an illustrative embodiment. The process illustrated in Figure is an example of one implementation for step 1304 in FIG. 13.

The process begins by generating a trap-assisted recombination lifetime based on a range of trap-assisted recombination lifetimes (step 1400). The process identifies an estimate of detected photons based on the trap-assisted recombination lifetime and simulation information (step 1402).

The process then identifies an amount of error based on the difference between the estimate of detected photons and detected photons in data (step 1404). The detected photons are an example of detected photons 414 emitted from material 104. In the illustrative example, steps 1400-1404 may be repeated until the process finds the trap-assisted recombination lifetime in range of trap-assisted recombination lifetimes for which the error is closest to zero.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step. For example, one or more of the blocks may be implemented as program code, in hardware, or a combination of the program code and hardware. When implemented in hardware, the hardware may, for example, take the form of integrated circuits that are manufactured or configured to perform one or more operations in the flowcharts or block diagrams. When implemented as a combination of program code and hardware, the implementation may take the form of firmware.

In some alternative implementations of an illustrative embodiment, the function or functions noted in the blocks may occur out of the order noted in the figures. For example, in some cases, two blocks shown in succession may be performed substantially concurrently, or the blocks may sometimes be performed in the reverse order, depending upon the functionality involved. Also, other blocks may be added in addition to the illustrated blocks in a flowchart or block diagram. For example, simulation of the recombination of carriers in FIG. 13 may also include simulating auger recombination.

Figure 15:
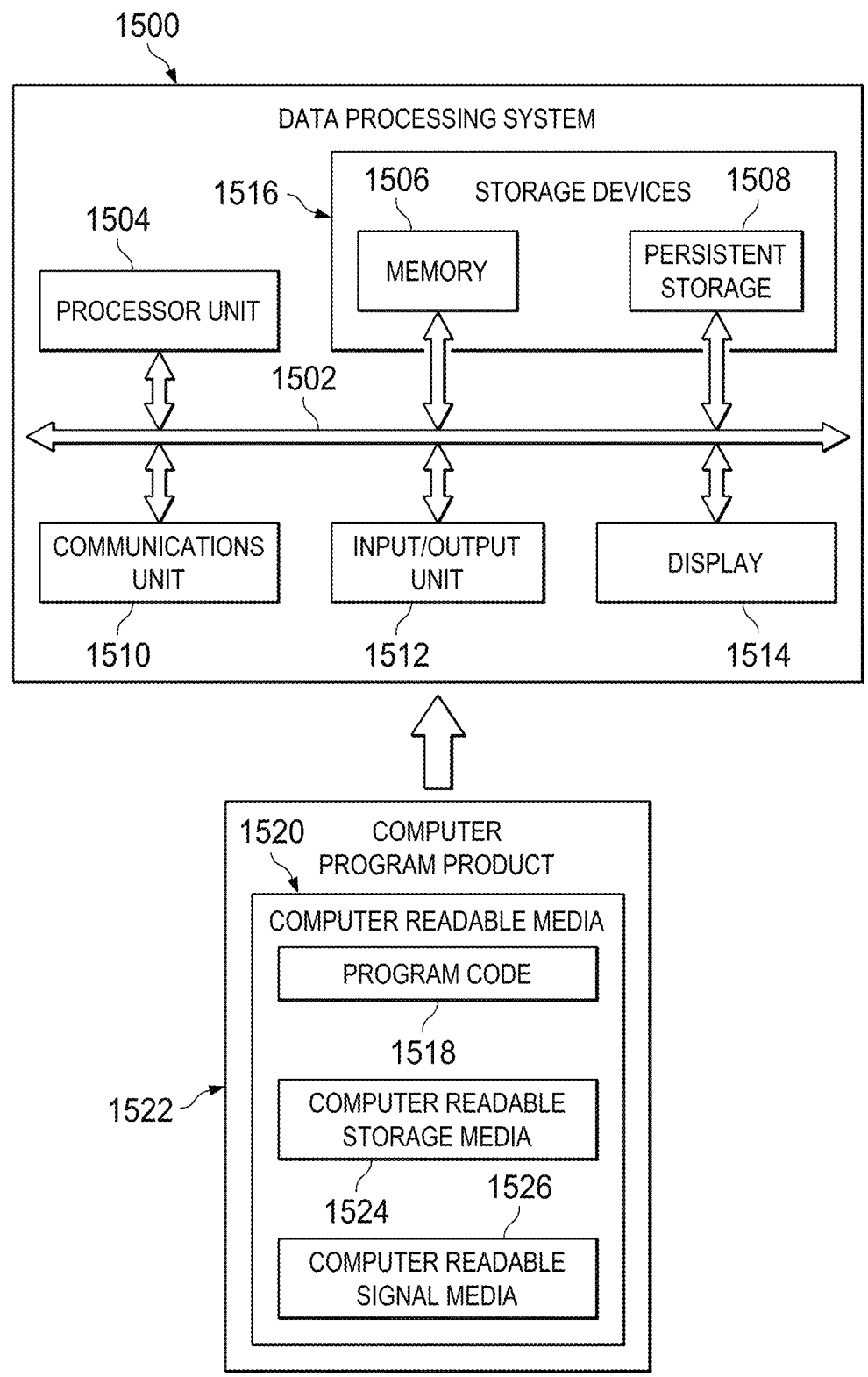
FIG. 15 is an illustration of a block diagram of a data processing system in accordance with an illustrative embodiment.

Turning now to FIG. 15, an illustration of a block diagram of a data processing system is depicted in accordance with an illustrative embodiment. Data processing system 1500 may be used to implement computer system 216 in FIG. 2. In this illustrative example, data processing system 1500 includes communications framework 1502, which provides communications between processor unit 1504, memory 1506, persistent storage 1508, communications unit 1510, input/output (I/O) unit 1512, and display 1514. In this example, communications framework 1502 may take the form of a bus system.

Processor unit 1504 serves to execute instructions for software that may be loaded into memory 1506. Processor unit 1504 may be a number of processors, a multi-processor core, or some other type of processor, depending on the particular implementation.

Memory 1506 and persistent storage 1508 are examples of storage devices 1516. A storage device is any piece of hardware that is capable of storing information, such as, for example, without limitation, at least one of data, program code in functional form, or other suitable information either on a temporary basis, a permanent basis, or both on a temporary basis and a permanent basis. Storage devices 1516 may also be referred to as computer readable storage devices in these illustrative examples. Memory 1506, in these examples, may be, for example, a random access memory or any other suitable volatile or non-volatile storage device. Persistent storage 1508 may take various forms, depending on the particular implementation.

For example, persistent storage 1508 may contain one or more components or devices. For example, persistent storage 1508 may be a hard drive, a flash memory, a rewritable optical disk, a rewritable magnetic tape, or some combination of the above. The media used by persistent storage 1508 also may be removable. For example, a removable hard drive may be used for persistent storage 1508.

Communications unit 1510, in these illustrative examples, provides for communications with other data processing systems or devices. In these illustrative examples, communications unit 1510 is a network interface card.

Input/output unit 1512 allows for input and output of data with other devices that may be connected to data processing system 1500. For example, input/output unit 1512 may provide a connection for user input through at least of a keyboard, a mouse, or some other suitable input device. Further, input/output unit 1512 may send output to a printer. Display 1514 provides a mechanism to display information to a user.

Instructions for at least one of the operating system, applications, or programs may be located in storage devices 1516, which are in communication with processor unit 1504 through communications framework 1502. The processes of the different embodiments may be performed by processor unit 1504 using computer-implemented instructions, which may be located in a memory, such as memory 1506.

These instructions are referred to as program code, computer usable program code, or computer readable program code that may be read and executed by a processor in processor unit 1504. The program code in the different embodiments may be embodied on different physical or computer readable storage media, such as memory 1506 or persistent storage 1508.

Program code 1518 is located in a functional form on computer readable media 1520 that is selectively removable and may be loaded onto or transferred to data processing system 1500 for execution by processor unit 1504. Program code 1518 and computer readable media 1520 form computer program product 1522 in these illustrative examples. In one example, computer readable media 1520 may be computer readable storage media 1524 or computer readable signal media 1526.

In these illustrative examples, computer readable storage media 1524 is a physical or tangible storage device used to store program code 1518 rather than a medium that propagates or transmits program code 1518. Alternatively, program code 1518 may be transferred to data processing system 1500 using computer readable signal media 1526. Computer readable signal media 1526 may be, for example, a propagated data signal containing program code 1518. For example, computer readable signal media 1526 may be at least one of an electromagnetic signal, an optical signal, or any other suitable type of signal. These signals may be transmitted over at least one of communications links, such as wireless communications links, optical fiber cable, coaxial cable, a wire, or any other suitable type of communications link.

The different components illustrated for data processing system 1500 are not meant to provide architectural limitations to the manner in which different embodiments may be implemented. The different illustrative embodiments may be implemented in a data processing system including components in addition to or in place of those illustrated for data processing system 1500. Other components shown in FIG. 15 can be varied from the illustrative examples shown. The different embodiments may be implemented using any hardware device or system capable of running program code 1518.

Thus, the illustrative embodiments provide a method and apparatus for identifying carrier lifetimes for materials for use in optical detectors. In this illustrative example, inspection system 102 may be used to identify carrier lifetimes for the material used in an infrared detector device such as an infrared focal plane array. In other illustrative examples, inspection system 102 may be used to identify carrier lifetimes for a material used in other types of optical devices such as those used to detect visible light, ultraviolet light, or other wavelengths of radiation.

With an illustrative example, inspection of the material may be performed sooner in manufacturing. By identifying carrier lifetimes from photons emitted in response to light directed onto the material, inspecting materials using an illustrative example occurs at a time in manufacturing sooner than is currently performed. This type of inspection allows for inspecting the material at a sooner point in time in manufacturing than when inspections currently occur. The technical problem of wasting resources and time that occurs when infrared detector devices are currently tested is reduced or avoided. A technical effect occurs in which manufacturing infrared detector devices may occur more quickly and at a lower cost as compared to currently used manufacturing processes that inspect infrared detector devices when they are complete.

The description of the different illustrative embodiments has been presented for purposes of illustration and description and is not intended to be exhaustive or limited to the embodiments in the form disclosed. The different illustrative examples describe components that perform actions or operations. In an illustrative embodiment, a component may be configured to perform the action or operation described. For example, the component may have a configuration or design for a structure that provides the component an ability to perform the action or operation that is described in the illustrative examples as being performed by the component.

Many modifications and variations will be apparent to those of ordinary skill in the art. Further, different illustrative embodiments may provide different features as compared to other desirable embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method for identifying carrier lifetimes, the method comprising:
    sending a beam of light to a group of locations on a material for an optical device;
    detecting photons emitted from the material at each of the group of locations; and
    identifying a carrier lifetime for each of the group of locations based on the photons detected from each of the group of locations.

2. The method of claim 1, wherein the identifying step comprises:
    identifying the carrier lifetime for each of the group of locations based on the photons detected from each of the group of locations and a simulation of the photons emitted from the material at each of the group of locations.

3. The method of claim 1, wherein the identifying step comprises:
    simulating trap-assisted recombination for the material in response to the beam of light on the material in the simulation;
    varying the trap-assisted recombination in the simulation to find a level of the trap-assisted recombination that causes the photons emitted from the material to match the photons detected within a desired level of variance; and
    identifying the carrier lifetime for each of the group of locations based on the trap-assisted recombination identified.

4. The method of claim 3, wherein identifying the carrier lifetime for each of the group of locations based on the photons detected from each of the group of locations further comprises:
    simulating a radiative recombination occurring in response to the beam of light in the simulation.

5. The method of claim 1 further comprising:
    generating a map of carrier lifetimes for the material from the identification of the carrier lifetime for each of the group of locations.

6. The method of claim 1 further comprising:
    placing the material into an interior of a vessel; and
    sending the beam of light on to the material in the interior of the vessel through a window in the vessel.

7. The method of claim 6 further comprising:
    applying a vacuum to the vessel.

8. The method of claim 1, wherein the optical device is an infrared detector device and further comprising:
    cooling the material to a temperature at which the infrared detection device incorporating the material operates.

9. The method of claim 1, wherein the beam of light is a laser beam.

10. The method of claim 1, wherein the material is located in one of a wafer, a focal plane array, an infrared detector device, a chip, or the chip with an integrated circuit.

11. An apparatus comprising:
    an inspection system that sends a beam of light to a group of locations on a material for an optical device;
    detects photons emitted from the material at each of the group of locations; and identifies a carrier lifetime for each of the group of locations based on the photons detected from each of the group of locations.

12. The apparatus of claim 11, wherein in identifying the carrier lifetime for each of the group of locations based on the photons detected from each of the group of locations, the inspection system identifies the carrier lifetime for each of the group of locations based on the photons detected from each of the group of locations and a simulation of the photons emitted from the material at each of the group of locations.

13. The apparatus of claim 11, wherein in identifying the carrier lifetime for each of the group of locations based on the photons detected from each of the group of locations, the inspection system simulates trap-assisted recombination for the material in response to the beam of light on the material in the simulation; varies the trap-assisted recombination in the simulation to find a level of the trap-assisted recombination that causes the photons emitted from the material to match the photons detected within a desired level of variance; and identifies the carrier lifetime for each of the group of locations based on the trap-assisted recombination identified.

14. The apparatus of claim 13, wherein in identifying the carrier lifetime for each of the group of locations based on the photons detected from each of the group of locations, the inspection system simulates a radiative recombination occurring in response to the beam of light in the simulation.

15. The apparatus of claim 11, wherein the inspection system generates a map of carrier lifetimes for the material from the identification of the carrier lifetime for each of the group of locations.

16. The apparatus of claim 11, wherein the inspection system comprises:
    a test platform that is configured to hold the material for the optical device;
    a light source that sends the beam of light to the group of locations on the material held by the test platform;
    a detector that detects the photons emitted from the material at each of the group of locations in response to the beam of light being sent to the group of locations; and
    an analyzer that identifies the carrier lifetime for each of the group of locations based on the photons detected from each of the group of locations.

17. The apparatus of claim 11, wherein the inspection system sends the beam of light on to the material in an interior of a vessel through a window in the vessel when the material is placed into the interior of the vessel.

18. The apparatus of claim 16, wherein the test platform is a vessel and the inspection system applies a vacuum to the vessel and cools the material to a temperature at which the optical device incorporating the material operates.

19. The apparatus of claim 11, wherein the material is located in one of a wafer, a focal plane array, an infrared detector device, a chip, or the chip with an integrated circuit.

20. An inspection system comprising:
    a test platform that is configured to hold a material for an optical device;
    a light source that sends a beam of light to a group of locations on the material held by the test platform;
    a detector that detects photons emitted from the material at each of the group of locations in response to the beam of light being sent to the group of locations; and
    an analyzer that identifies a carrier lifetime for each of the group of locations based on the photons detected from each of the group of locations and a simulation of the photons emitted from the material at each of the group of locations.

21. The inspection system of claim 20, wherein in the carrier lifetime for each of the group of locations, the analyzer simulates trap-assisted recombination for the material in response to the beam of light on the material in the simulation; varies the trap-assisted recombination in the simulation to find a level of the trap-assisted recombination that causes the photons emitted from the material to match the photons detected within a desired level of variance; and identifies the carrier lifetime for each of the group of locations based on the trap-assisted recombination identified.

22. A method for inspecting a material for an infrared detection device, the method comprising:
    placing the material for the infrared detection device into an interior of a vessel;
    applying a vacuum to the vessel;
    cooling the material to a temperature at which the infrared detection device incorporating the material operates;
    sending a laser beam through a window in the vessel onto the material in the vessel to form a spot for the laser beam on the material;
    moving the spot to locations on the material;
    detecting photons emitted from the material at each of the locations to which the spot moves; and
    identifying a carrier lifetime for each of the locations based on the photons detected from each of the locations and a simulation of the photons emitted from the material at each of the locations.

23. The method of claim 22, wherein the identifying step comprises:
    simulating trap-assisted recombination for the material in response to the laser beam on the material in the simulation;
    varying the trap-assisted recombination in the simulation to find a level of the trap-assisted recombination that causes the photons emitted from the material to match the photons detected within a desired level of variance; and
    identifying the carrier lifetime for each of a group of locations based on the trap-assisted recombination identified.

\* \* \* \* \*